(12) United States Patent
Nageri et al.

(10) Patent No.: US 10,814,127 B2
(45) Date of Patent: Oct. 27, 2020

(54) SLOTTED SLEEVE NEUROSTIMULATION DEVICE

(71) Applicant: Boston Scientific Neuromodulation Corporation, Valencia, CA (US)

(72) Inventors: Ranjan Krishna Mukhari Nageri, Valencia, CA (US); Tiffany Shen, Laguna Niguel, CA (US)

(73) Assignee: BOSTON SCIENTIFIC NEUROMODULATION CORPORATION, Valencia, CA (US)

( * ) Notice: Subject to any disclaimer, the term of this patent is extended or adjusted under 35 U.S.C. 154(b) by 787 days.

(21) Appl. No.: 15/424,481

(22) Filed: Feb. 3, 2017

(65) Prior Publication Data

US 2017/0224982 A1 Aug. 10, 2017

Related U.S. Application Data

(60) Provisional application No. 62/292,093, filed on Feb. 5, 2016.

(51) Int. Cl.
 *A61N 1/05* (2006.01)
 *A61N 1/36* (2006.01)

(52) U.S. Cl.
 CPC ......... *A61N 1/0556* (2013.01); *A61N 1/0558* (2013.01); *A61N 1/3605* (2013.01)

(58) Field of Classification Search
 CPC .................................................. A61N 1/0556
 See application file for complete search history.

(56) References Cited

U.S. PATENT DOCUMENTS 3,769,984 A 11/1973 Muench
3,941,136 A 3/1976 Bucalo
(Continued)

FOREIGN PATENT DOCUMENTS

WO 98/37926 9/1998
WO 98/43701 10/1998
(Continued)

OTHER PUBLICATIONS

Rattay, F., "Analysis of Models for External Stimulation of Axons," IEEE Transactions on Biomedical Engineering, BME-33(10): 974-977, 1986.
(Continued)

*Primary Examiner* — Rex R Holmes
*Assistant Examiner* — Jennifer L Ghand
(74) *Attorney, Agent, or Firm* — Lowe Graham Jones PLLC; Bruce E. Black

(57) ABSTRACT

An electrical stimulation lead for a target nerve includes a sleeve having an inner surface and an outer surface, the inner surface defines a nerve channel. A longitudinal slit extends from the outer surface to the nerve channel and along an entire length of the sleeve. A width of the slit retains the target nerve within the nerve channel when the sleeve is closed and releases the target nerve when open. A plurality of electrodes are disposed on the inner surface of the sleeve. A flexible transition element electrically couples a lead body to the plurality of electrodes. Upper and lower sections of the sleeve rotates about a common hinge line (e.g., like a clam shell) located directly opposite the longitudinal slit. The material along the common hinge line remains "elastic" when the sleeve is moved from closed to open, and vice-versa.

20 Claims, 7 Drawing Sheets

(56) References Cited

U.S. PATENT DOCUMENTS

| | | |
|---|---|---|
| 4,033,357 A | 7/1977 | Helland et al. |
| 4,135,518 A | 1/1979 | Dutcher |
| 4,257,428 A | 3/1981 | Barton et al. |
| 4,301,815 A | 11/1981 | Doring |
| 4,409,994 A | 10/1983 | Doring |
| 4,475,560 A | 10/1984 | Tarjan et al. |
| 4,506,679 A | 3/1985 | Mann |
| 4,542,753 A | 9/1985 | Brenman et al. |
| 4,585,005 A | 4/1986 | Lue et al. |
| 4,628,944 A | 12/1986 | MacGregor et al. |
| 4,702,254 A | 10/1987 | Zabara |
| 4,716,888 A | 1/1988 | Wesner |
| 4,722,353 A | 2/1988 | Sluetz |
| 4,796,643 A | 1/1989 | Nakazawa et al. |
| 4,867,164 A | 9/1989 | Zabara |
| 4,920,979 A | 5/1990 | Bullara |
| 4,934,368 A | 6/1990 | Lynch |
| 4,957,118 A | 9/1990 | Erlebacher |
| 5,025,807 A | 6/1991 | Zabara |
| 5,095,905 A | 3/1992 | Klepinski |
| 5,139,539 A | 8/1992 | Haynes, Jr. |
| 5,143,067 A | 9/1992 | Rise et al. |
| 5,193,539 A | 3/1993 | Schulman et al. |
| 5,193,540 A | 3/1993 | Schulman et al. |
| 5,239,540 A | 8/1993 | Rovira et al. |
| 5,251,634 A | 10/1993 | Weinberg |
| 5,257,634 A | 11/1993 | Kroll |
| 5,282,468 A | 2/1994 | Klepinski |
| 5,312,439 A | 5/1994 | Loeb |
| 5,314,457 A | 5/1994 | Jeutter et al. |
| 5,324,322 A | 6/1994 | Grill et al. |
| 5,324,327 A | 6/1994 | Cohen |
| 5,376,108 A | 12/1994 | Collins et al. |
| 5,405,367 A | 4/1995 | Schulman et al. |
| 5,433,735 A | 7/1995 | Zanakis et al. |
| 5,439,938 A | 8/1995 | Synder et al. |
| 5,454,840 A | 10/1995 | Krakovsky et al. |
| 5,480,420 A | 1/1996 | Hoegnelid et al. |
| 5,487,756 A | 1/1996 | Kallesoe et al. |
| 5,531,781 A | 7/1996 | Alferness et al. |
| 5,571,118 A | 11/1996 | Boutos |
| 5,741,319 A | 4/1998 | Woloszko et al. |
| 5,755,762 A | 5/1998 | Bush |
| 5,775,331 A | 7/1998 | Raymond et al. |
| 5,876,399 A | 3/1999 | Chia et al. |
| 5,919,220 A | 7/1999 | Stieglitz et al. |
| 5,922,015 A | 7/1999 | Schaldach et al. |
| 5,938,584 A | 8/1999 | Ardito et al. |
| 6,051,017 A | 4/2000 | Loeb et al. |
| 6,058,332 A | 5/2000 | Dahl |
| 6,061,596 A | 5/2000 | Richmond et al. |
| 6,151,526 A | 11/2000 | Tziviskos |
| 6,175,710 B1 | 1/2001 | Kamaji et al. |
| 6,175,764 B1 | 1/2001 | Loeb et al. |
| 6,181,965 B1 | 1/2001 | Loeb et al. |
| 6,181,969 B1 | 1/2001 | Gord |
| 6,181,973 B1 | 1/2001 | Ceron et al. |
| 6,185,452 B1 | 2/2001 | Schulman et al. |
| 6,185,455 B1 | 2/2001 | Loeb et al. |
| 6,188,932 B1 | 2/2001 | Lindegren |
| 6,201,994 B1 | 3/2001 | Warman et al. |
| 6,214,032 B1 | 4/2001 | Loeb et al. |
| 6,224,450 B1 | 5/2001 | Norton |
| 6,271,094 B1 | 8/2001 | Boyd et al. |
| 6,278,897 B1 | 8/2001 | Rutten et al. |
| 6,292,703 B1 | 9/2001 | Meier et al. |
| 6,295,944 B1 | 10/2001 | Lovett |
| 6,308,105 B1 | 10/2001 | Duysens et al. |
| 6,315,721 B2 | 11/2001 | Schulman et al. |
| 6,364,278 B1 | 4/2002 | Lin et al. |
| 6,391,985 B1 | 5/2002 | Goode et al. |
| 6,456,866 B1 | 9/2002 | Tyler et al. |
| 6,463,335 B1 | 10/2002 | Munch et al. |
| 6,516,227 B1 | 2/2003 | Meadows et al. |
| 6,582,441 B1 | 6/2003 | He et al. |
| 6,584,363 B2 | 6/2003 | Heil, Jr. et al. |
| 6,609,029 B1 | 8/2003 | Mann et al. |
| 6,609,032 B1 | 8/2003 | Woods et al. |
| 6,643,546 B2 | 11/2003 | Mathis et al. |
| 6,650,943 B1 | 11/2003 | Whitehurst et al. |
| 6,735,474 B1 | 5/2004 | Loeb et al. |
| 6,741,892 B1 | 5/2004 | Meadows et al. |
| 6,788,975 B1 | 9/2004 | Whitehurst et al. |
| 7,003,352 B1 | 2/2006 | Whitehurst |
| 7,006,875 B1 | 2/2006 | Kuzma et al. |
| 7,203,548 B2 | 4/2007 | Whitehurst et al. |
| 7,244,150 B1 | 7/2007 | Brase et al. |
| 7,248,930 B1 | 7/2007 | Woloszko et al. |
| 7,292,890 B2 | 11/2007 | Whitehurst et al. |
| 7,437,193 B2 | 10/2008 | Parramon et al. |
| 7,450,997 B1 | 11/2008 | Pianca et al. |
| 7,460,913 B2 | 12/2008 | Kuzma et al. |
| 7,584,004 B2 | 9/2009 | Caparso et al. |
| 7,596,414 B2 | 9/2009 | Whitehurst et al. |
| 7,610,103 B2 | 10/2009 | Whitehurst et al. |
| 7,672,734 B2 | 3/2010 | Anderson et al. |
| 7,706,892 B2 | 4/2010 | Colvin et al. |
| 7,761,165 B1 | 7/2010 | He et al. |
| 7,783,359 B2 | 8/2010 | Meadows |
| 7,783,362 B2 | 8/2010 | Whitehurst et al. |
| 7,792,590 B1 | 9/2010 | Pianca et al. |
| 7,809,446 B2 | 10/2010 | Meadows |
| 7,840,279 B2 | 11/2010 | He |
| 7,949,395 B2 | 5/2011 | Kuzma |
| 7,953,498 B1 | 5/2011 | Carbunaru et al. |
| 7,974,706 B2 | 7/2011 | Moffitt et al. |
| 8,019,443 B2 | 9/2011 | Schleicher et al. |
| 8,155,757 B1 | 4/2012 | Neisz et al. |
| 8,175,710 B2 | 5/2012 | He |
| 8,224,450 B2 | 7/2012 | Brase |
| 8,271,094 B1 | 9/2012 | Moffitt et al. |
| 8,295,944 B2 | 10/2012 | Howard et al. |
| 8,364,278 B2 | 1/2013 | Pianca et al. |
| 8,391,985 B2 | 3/2013 | McDonald |
| 8,483,237 B2 | 7/2013 | Zimmermann et al. |
| 8,594,805 B2 | 11/2013 | Hincapie Ordonez et al. |
| 8,612,025 B2 | 12/2013 | Neisz et al. |
| 8,688,235 B1 | 4/2014 | Pianca et al. |
| 8,718,790 B2 | 5/2014 | Pianca |
| 8,768,488 B2 | 7/2014 | Barker |
| 8,818,524 B2 | 8/2014 | Hincapie Ordonez et al. |
| 8,831,742 B2 | 9/2014 | Pianca et al. |
| 8,849,422 B2 | 9/2014 | Pianca |
| 8,934,992 B2 | 1/2015 | Johnson et al. |
| 2003/0040785 A1 | 2/2003 | Maschino et al. |
| 2003/0045919 A1 | 3/2003 | Swoyer et al. |
| 2003/0074039 A1 | 4/2003 | Puskas |
| 2003/0078623 A1 | 4/2003 | Weinberg et al. |
| 2003/0114905 A1 | 6/2003 | Kuzma |
| 2003/0199938 A1 | 10/2003 | Smits et al. |
| 2003/0236558 A1 | 12/2003 | Whitehurst et al. |
| 2004/0010303 A1 | 1/2004 | Bolea et al. |
| 2004/0034401 A1 | 2/2004 | Dahlberg et al. |
| 2004/0049240 A1* | 3/2004 | Gerber ............... A61N 1/36071 607/40 |
| 2004/0059392 A1 | 3/2004 | Parramon et al. |
| 2004/0111139 A1 | 6/2004 | McCreery |
| 2004/0230280 A1 | 11/2004 | Cates et al. |
| 2005/0010265 A1 | 1/2005 | Baru Fassio et al. |
| 2005/0065589 A1 | 3/2005 | Schneider et al. |
| 2005/0177220 A1 | 8/2005 | Iaizzo et al. |
| 2005/0182472 A1 | 8/2005 | Wahlstrom et al. |
| 2006/0161204 A1 | 7/2006 | Colvin et al. |
| 2006/0184204 A1 | 8/2006 | He |
| 2006/0212075 A1 | 9/2006 | Marnfeldt |
| 2006/0241737 A1 | 10/2006 | Tockman et al. |
| 2006/0282145 A1 | 12/2006 | Caparso et al. |
| 2007/0150036 A1 | 6/2007 | Anderson |
| 2007/0219595 A1 | 9/2007 | He |
| 2008/0046055 A1* | 2/2008 | Durand ............... A61N 1/0556 607/118 |
| 2008/0071320 A1 | 3/2008 | Brase |
| 2009/0187222 A1 | 7/2009 | Barker |

(56) References Cited

U.S. PATENT DOCUMENTS

| | | | |
|---|---|---|---|
| 2009/0210042 A1* | 8/2009 | Kowalczewski | A61B 5/04001 607/118 |
| 2009/0276021 A1 | 11/2009 | Meadows et al. | |
| 2009/0287271 A1 | 11/2009 | Blum et al. | |
| 2009/0287272 A1 | 11/2009 | Kokones et al. | |
| 2009/0287273 A1 | 11/2009 | Carlton et al. | |
| 2009/0287467 A1 | 11/2009 | Sparks et al. | |
| 2010/0049276 A1 | 2/2010 | Blum et al. | |
| 2010/0076535 A1 | 3/2010 | Pianca et al. | |
| 2010/0168831 A1* | 7/2010 | Korivi | A61N 1/0556 607/118 |
| 2010/0241207 A1 | 9/2010 | Bluger | |
| 2010/0268298 A1 | 10/2010 | Moffitt et al. | |
| 2010/0298916 A1 | 11/2010 | Rabischong et al. | |
| 2010/0312320 A1* | 12/2010 | Faltys | A61N 1/0556 607/118 |
| 2011/0004267 A1 | 1/2011 | Meadows et al. | |
| 2011/0005069 A1 | 1/2011 | Pianca | |
| 2011/0078900 A1 | 4/2011 | Pianca et al. | |
| 2011/0130803 A1 | 6/2011 | McDonald | |
| 2011/0130817 A1 | 6/2011 | Chen | |
| 2011/0130818 A1 | 6/2011 | Chen | |
| 2011/0238129 A1 | 9/2011 | Moffitt et al. | |
| 2011/0313500 A1 | 12/2011 | Barker et al. | |
| 2012/0016378 A1 | 1/2012 | Pianca et al. | |
| 2012/0046710 A1 | 2/2012 | Digiore et al. | |
| 2012/0071949 A1 | 3/2012 | Pianca et al. | |
| 2012/0165911 A1 | 6/2012 | Pianca | |
| 2012/0185027 A1 | 7/2012 | Pianca et al. | |
| 2012/0197375 A1 | 8/2012 | Pianca et al. | |
| 2012/0203320 A1 | 8/2012 | Digiore et al. | |
| 2012/0203321 A1 | 8/2012 | Moffitt et al. | |
| 2012/0277819 A1* | 11/2012 | Cowley | A61N 1/0556 607/45 |
| 2012/0316615 A1 | 12/2012 | Digiore et al. | |
| 2013/0023974 A1 | 1/2013 | Amrani | |
| 2013/0105071 A1 | 5/2013 | Digiore et al. | |
| 2013/0172973 A1 | 7/2013 | Tockman et al. | |
| 2013/0197424 A1 | 8/2013 | Bedenbaugh | |
| 2013/0197602 A1 | 8/2013 | Pianca et al. | |
| 2013/0261684 A1 | 10/2013 | Howard | |
| 2013/0317518 A1 | 11/2013 | Govea | |
| 2013/0317587 A1 | 11/2013 | Barker | |
| 2013/0325091 A1 | 12/2013 | Pianca et al. | |
| 2014/0039587 A1 | 2/2014 | Romero | |
| 2014/0074213 A1 | 3/2014 | Neisz et al. | |
| 2014/0128950 A1* | 5/2014 | Thota | A61N 1/05 607/116 |
| 2014/0228905 A1* | 8/2014 | Bolea | A61N 1/0556 607/42 |
| 2014/0277284 A1 | 9/2014 | Chen et al. | |
| 2014/0353001 A1 | 12/2014 | Romero et al. | |
| 2014/0358207 A1 | 12/2014 | Romero | |
| 2014/0358209 A1 | 12/2014 | Romero et al. | |
| 2014/0358210 A1 | 12/2014 | Howard et al. | |
| 2015/0018915 A1 | 1/2015 | Leven | |
| 2015/0021817 A1 | 1/2015 | Romero et al. | |
| 2015/0045864 A1 | 2/2015 | Howard | |
| 2015/0066120 A1 | 3/2015 | Govea | |
| 2015/0119965 A1 | 4/2015 | Govea | |
| 2015/0151113 A1 | 6/2015 | Govea et al. | |
| 2015/0202433 A1 | 7/2015 | Franke et al. | |
| 2015/0202446 A1 | 7/2015 | Franke et al. | |
| 2015/0366467 A1 | 12/2015 | De Kock et al. | |
| 2017/0224982 A1 | 8/2017 | Nageri et al. | |

FOREIGN PATENT DOCUMENTS

| | | |
|---|---|---|
| WO | 2008019483 | 2/2008 |
| WO | 2008048471 | 4/2008 |
| WO | 2013188871 | 12/2013 |

OTHER PUBLICATIONS

U.S. Appl. No. 15/601,838, filed May 22, 2017.
U.S. Appl. No. 15/608,573, filed May 30, 2017.
U.S. Appl. No. 62/429,650, filed Dec. 2, 2016.
U.S. Appl. No. 15/656,734, filed Jul. 21, 2017.
Rozman et al., "Selective Stimulation of Autonomic Nerves and Recording of Electroneurograms in a Canine Model," Artificial Organs, 21(8): 592-596, 2008.
Polasek et al., "Stimulation Stability and Selectivity of Chronically Implanted Multicontact Nerve Cuff Electrodes in the Human Upper Extremity," IEEE Transactions on Neural Systems and Rehabilitation Engineering, vol. 17, No. 5, 428-437, Oct. 2009.
Plachta et al., "Blood pressure control with selective vagal nerve stimulation and minimal side effects," J. Neural Eng. 11 (2014) 036011 (15pp), 2014.
U.S. Appl. No. 12/177,823, Entitled: Lead With Transition and Methods of Manufacture and Use, Inventor: Pianca et al., filed Jul. 22, 2008, 22 pages.
U.S. Appl. No. 13/750,725, Entitled: Systems and Methods for Identifying the Circumferential Positioning of Electrodes of Leads for Electrical Stimulation Systems, Inventor: Pianca et al., filed Jan. 25, 2013, 36 pages.
U.S. Appl. No. 62/292,093, Entitled: Slotted Sleeve Neurostimulation Device, Inventor: Ranjan Krishna Mukhari Nageri et al., filed Feb. 5, 2016, 32 pages.
U.S. Appl. No. 62/297,616, Entitled: Electrical Stimulation Cuff Devices and Systems, Inventor: Ranjan Mukhari Nageri et al., filed Feb. 19, 2016, 34 pages.
U.S. Appl. No. 15/436,544, Entitled: Electrical Stimulation Cuff Devices and Systems, Inventor: Govea et al., filed Feb. 17, 2017, 31 pages.

* cited by examiner

SLOTTED SLEEVE NEUROSTIMULATION DEVICE

CROSS-REFERENCE TO RELATED APPLICATIONS

This application claims the benefit under 35 U.S.C. § 119(e) of U.S. Provisional Patent Application Ser. No. 62/292,093, filed Feb. 5, 2016, which is incorporated herein by reference.

FIELD

The present invention is directed to the area of implantable electrical stimulation devices and methods of making and implanting the same. The present invention is also directed to slotted sleeve electrical stimulation devices, as well as methods of making and implanting the same.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients. Stimulation of the brain, such as deep brain stimulation, can be used to treat a variety of diseases or disorders.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

In one embodiment, an electrical stimulation lead for stimulating a target nerve includes an elongated sleeve having an inner surface and an outer surface, the inner surface defining a nerve channel, the sleeve further having a longitudinal slit extending from the outer surface to the nerve channel and further extending along an entire length of the sleeve. The lead further includes at least one suture tab having opposing surfaces defined by the longitudinal slit and the suture tab extends from the sleeve. The electrical stimulation lead further includes a plurality of electrodes disposed on the inner surface of the sleeve; a lead body; and a flexible transition element configured to electrically couple the lead body to the plurality of electrodes.

In at least some embodiments, the plurality of electrodes have a shape complementary to the inner surface of the sleeve. For opening and closing in the clam shell manner, the sleeve includes an elastic hinge line that cooperates with the longitudinal slit when the sleeve is manipulated to receive the target into the nerve channel. A width of the slit operates to retain the target nerve within the nerve channel when the sleeve is in a closed position and operates to receive or release the target nerve when the sleeve is in an open position (e.g., in the clam shell manner).

In at least some embodiments, the sleeve includes tapered end portions. The transition element takes the form of a ribbon cable having one or more bellowed portions for strain relief.

In another embodiment, an electrical stimulation system includes the electrical stimulation lead described above and further includes a control module and a connector. The control module is coupled to the electrical stimulation lead and includes a housing and an electronic subassembly disposed in the housing. The connector receives the electrical stimulation lead, and includes a proximal end, a distal end, and a longitudinal length. The connector further includes a connector housing that defines a port at the distal end of the connector, such that the port receives the proximal end of the lead body of the electrical stimulation lead. A plurality of connector contacts disposed in the connector housing couple to at least one of a plurality of terminals disposed on a proximal end of the lead body of the electrical stimulation lead. In at least some embodiments, a lead extension couples to both the electrical stimulation lead and the control module.

In yet another embodiment, an electrical stimulation lead for stimulating a target nerve includes an elongated sleeve having a first portion and a second portion, in which the first portion is hingedly coupled to the second portion. The sleeve has an inner surface that continually extends from the first portion to the second portion and an outer surface that continually extends from the first portion to the second portion. The inner surface defines a nerve channel for receiving the target nerve. The sleeve further includes a longitudinal slit extending from the outer surface to the nerve channel and also extending along an entire length of the sleeve. A section of the first portion hingedly moves relative to a section of the second portion, such that the sleeve opens in a clam shell manner, to receive the target nerve into the nerve channel. The sleeve also has tapered end portions. The electrical stimulation lead further includes a plurality of electrodes disposed on the inner surface of the sleeve; a lead body; and a ribbon cable that electrically couples the lead body to the plurality of electrodes.

In at least some embodiments, the section of the first portion rotates relative to the section of the second portion relative to a common hinge line (e.g., like a clam shell) located opposite the longitudinal slit. The material along the common hinge line remains in a mechanically elastic range when the sleeve is moved from a closed position to an open position.

In at least some embodiments, the lead further includes at least one suture tab having opposing surfaces defined by the longitudinal slit and the suture tab extends from the sleeve. The ribbon cable may include one or more bellowed portions for strain relief.

In further embodiments, an electrical stimulation system includes the electrical stimulation lead of claim described above, a control module and a connector. The control module is coupled to the electrical stimulation lead and includes a housing and an electronic subassembly disposed in the housing. The connector receives the electrical stimulation lead. The connector includes a proximal end, a distal end, and a longitudinal length. The connector further includes a connector housing that defines a port at the distal end of the connector. The port receives a proximal end of the lead body of the electrical stimulation lead. A plurality of connector contacts are disposed in the connector housing and operate to couple with at least one of a plurality of terminals disposed on the proximal end of the lead body. At least in some embodiments, the electrical stimulation system also includes a lead extension coupleable to both the electrical stimulation lead and the control module.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to implantable sleeve electrical stimulation devices, as well as methods of making and using the same.

Suitable implantable electrical stimulation systems include, but are not limited to, a least one lead with one or more electrodes disposed along a distal end of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,203,548; 7,244,150; 7,450,997; 7,596,414; 7,610,103; 7,672,734; 7,761,165; 7,783,359; 7,792,590; 7,809,446; 7,949,395; 7,974,706; 6,175,710; 6,224,450; 6,271,094; 6,295,944; 6,364,278; and 6,391,985; U.S. Patent Applications Publication Nos. 2007/0150036; 2009/0187222; 2009/0276021; 2010/0076535; 2010/0268298; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; and 2013/0105071; and U.S. patent application Ser. Nos. 12/177,823 and 13/750,725, all of which are incorporated by reference in their entireties.

Figure 1:
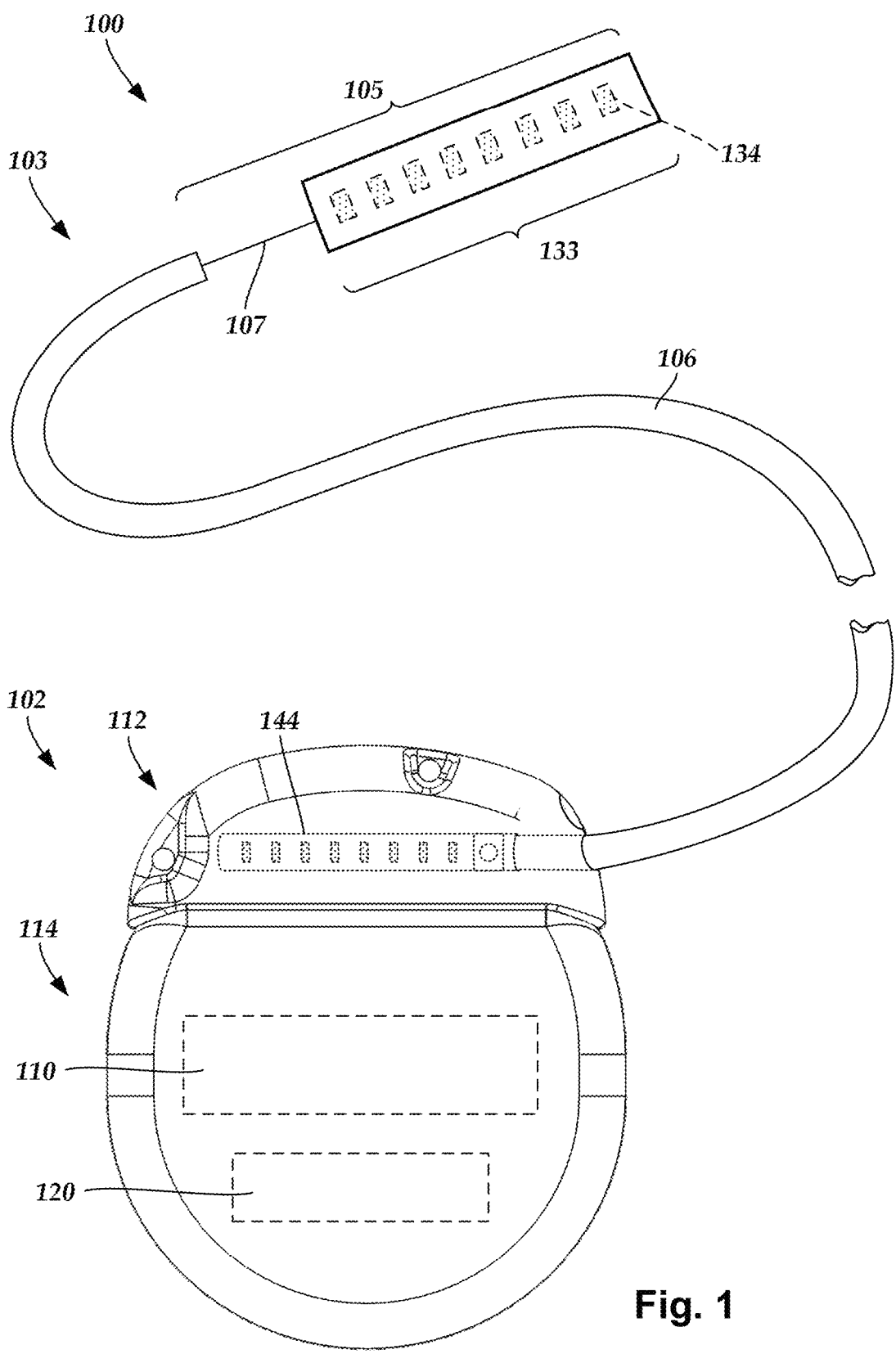
FIG. 1 is a schematic view of one embodiment of an electrical stimulation system that includes a lead electrically coupled to a control module according to an embodiment of the present invention.

FIG. 1 illustrates schematically one embodiment of an electrical stimulation system 100. The electrical stimulation system includes a control module (e.g., a stimulator or pulse generator) 102 and a lead 103 coupleable to the control module 102. The lead 103 includes a distal end portion 105, shown schematically, but will be described in detail below (e.g., in FIGS. 3-5). In one embodiment, the distal end portion 105 extends from a lead body 106 and includes a transition element 107 and a distal electrode array or electrodes 133, such as electrode 134, and an array of terminals (e.g., 210 in FIG. 2A-2B) disposed along the one or more lead bodies 106. In at least some embodiments, the lead is isodiametric along a longitudinal length of the lead body 106.

The lead 103 can be coupled to the control module 102 in any suitable manner. In at least some embodiments, the lead 103 couples directly to the control module 102. In at least some other embodiments, the lead 103 couples to the control module 102 via one or more intermediate devices (200 in FIGS. 2A-2B). For example, in at least some embodiments one or more lead extensions 224 (see e.g., FIG. 2B) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the electrical stimulation system 100 includes multiple elongated devices disposed between the lead 103 and the control module 102, the intermediate devices may be configured into any suitable arrangement.

The control module 102 typically includes a connector housing 112 and a sealed electronics housing 114. Stimulation circuitry 110 and an optional power source 120 are disposed in the electronics housing 114. A control module connector 144 is disposed in the connector housing 112. The control module connector 144 is configured and arranged to make an electrical connection between the lead 103 and the stimulation circuitry 110 of the control module 102.

The electrical stimulation system or components of the electrical stimulation system, including the lead body 106 and the control module 102, are typically implanted into the body of a patient. The electrical stimulation system can be used for a variety of applications including, but not limited to, brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium. The number of electrodes 134 in each array 133 may vary. For example, there can be two, four, six, eight, ten, twelve, fourteen, sixteen, or more electrodes 134. As will be recognized, other numbers of electrodes 134 may also be used.

The electrodes of the lead body 106 are typically disposed in, or separated by, a non-conductive, biocompatible material such as, for example, silicone, polyurethane, polyetheretherketone ("PEEK"), epoxy, and the like or combinations thereof. The lead body 106 may be formed in the desired shape by any process including, for example, molding (including injection molding), casting, and the like. The non-conductive material typically extends from the distal end of the lead body 106 to the proximal end of the lead body 106.

Figure 2A:
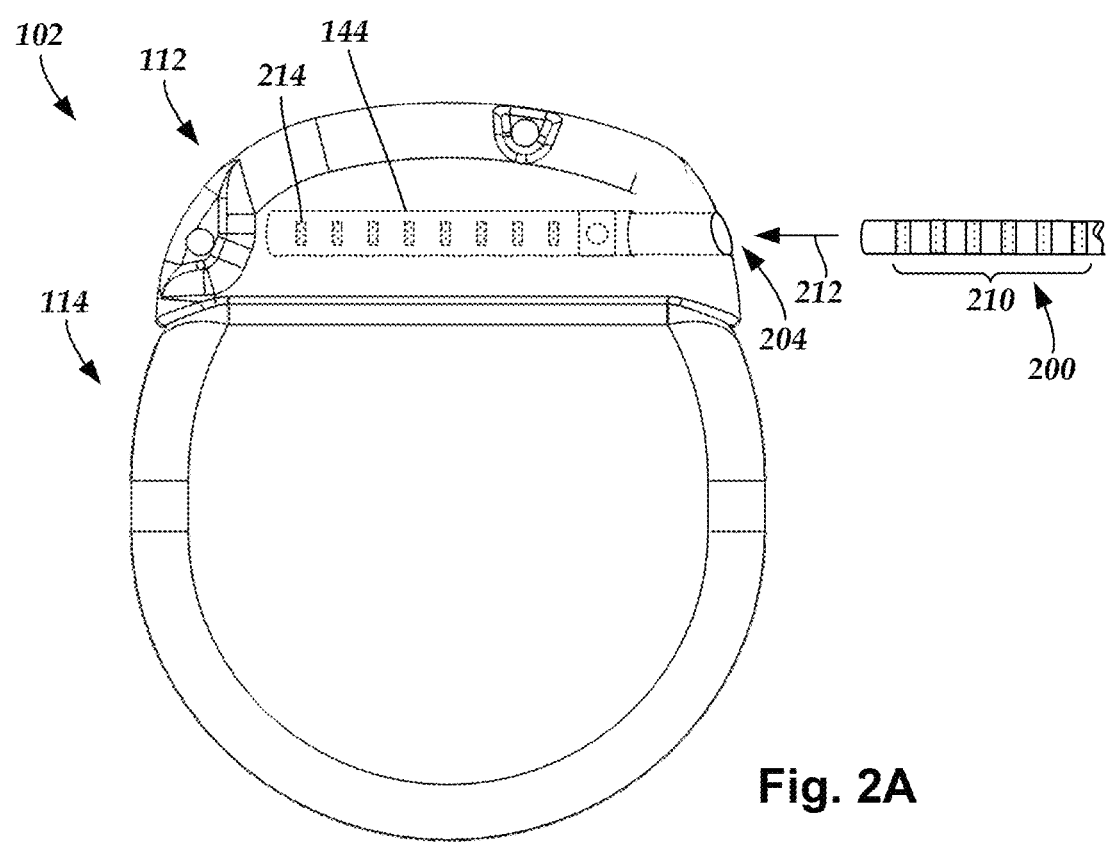
FIG. 2A is a schematic view of one embodiment of the control module of FIG. 1 configured and arranged to electrically couple to an elongated device according to an embodiment of the present invention.
Figure 2B:
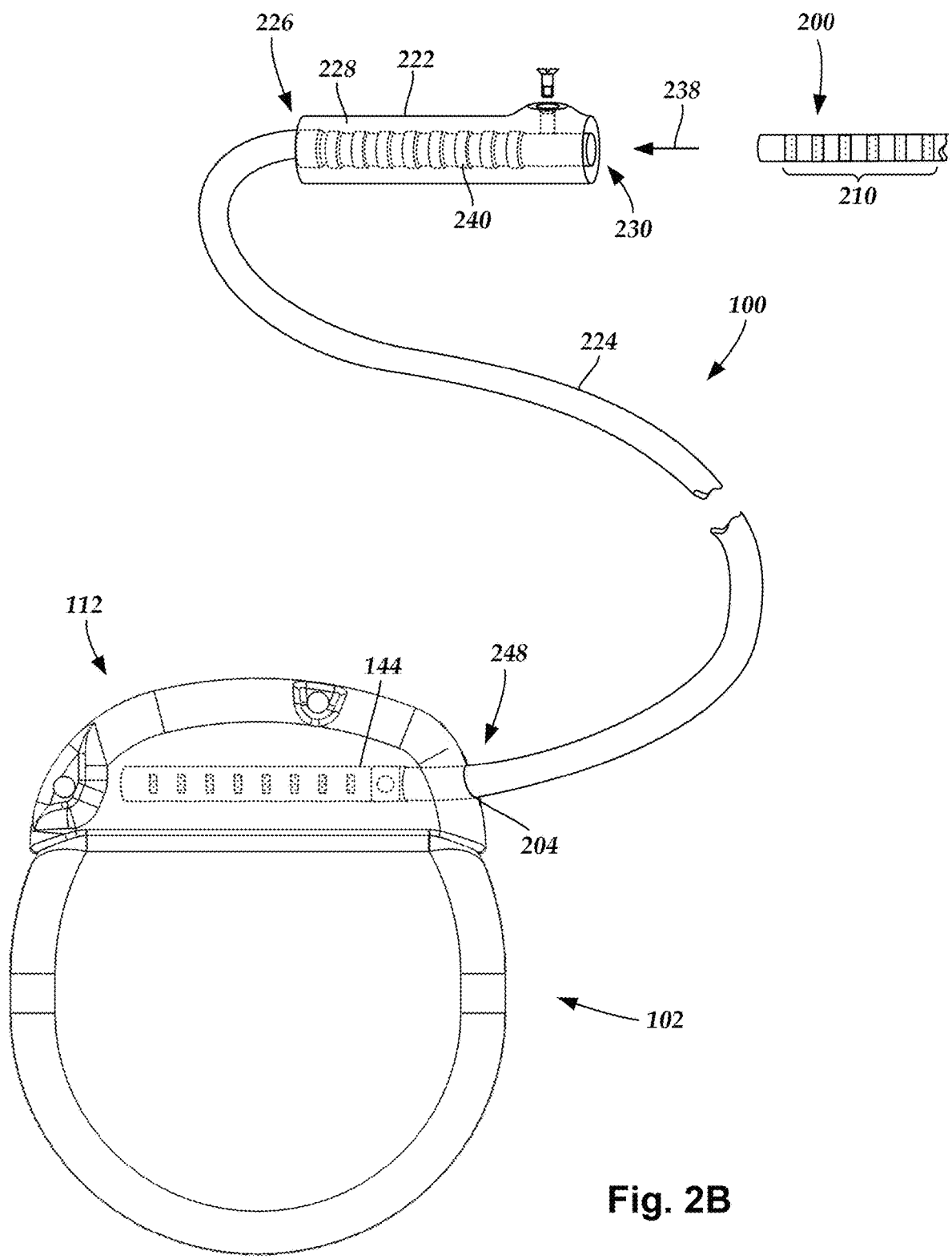
FIG. 2B is a schematic view of one embodiment of a lead extension configured and arranged to electrically couple the elongated device of FIG. 2A to the control module of FIG. 1 according to an embodiment of the present invention.

Terminals (e.g., 210 in FIGS. 2A-2B) are typically disposed along the proximal end of the lead body 106 of the electrical stimulation system 100 (as well as any splitters, lead extensions, adaptors, or the like) for electrical connection to corresponding connector contacts (e.g., 214 and 240 in FIG. 2B). The connector contacts are disposed in connectors (e.g., 144 in FIGS. 1-2B; and 222 in FIG. 2B) which, in turn, are disposed on, for example, the control module 102 (or a lead extension, a splitter, an adaptor, or the like). Electrically conductive wires, cables, or the like (not shown) extend from the terminals to the electrodes 134. Typically, one or more electrodes 134 are electrically coupled to each terminal. In at least some embodiments, each terminal is only connected to one electrode 134.

The electrically conductive wires ("conductors") may be embedded in the non-conductive material of the lead body 106 or can be disposed in one or more lumens (not shown) extending along the lead body 106. In some embodiments, there is an individual lumen for each conductor. In other embodiments, two or more conductors extend through a lumen. There may also be one or more lumens (not shown) that open at, or near, the proximal end of the lead body 106, for example, for inserting a stylet to facilitate placement of the lead body 106 within a body of a patient. Additionally, there may be one or more lumens (not shown) that open at, or near, the distal end of the lead body 106, for example, for infusion of drugs or medication into the site of implantation of the lead body 106. In at least one embodiment, the one or more lumens are flushed continually, or on a regular basis, with saline, epidural fluid, or the like. In at least some embodiments, the one or more lumens are permanently or removably sealable at the distal end.

FIG. 2A is a schematic side view of one embodiment of a proximal end of one or more elongated devices 200 configured and arranged for coupling to one embodiment of the control module connector 144. The one or more elongated devices may include, for example, the lead body 106, one or more intermediate devices (e.g., the lead extension 224 of FIG. 2B, an adaptor, or the like or combinations thereof), or a combination thereof.

The control module connector 144 defines at least one port into which a proximal end of the elongated device 200 can be inserted, as shown by directional arrow 212. In FIG. 2A (and in other figures), the connector housing 112 is shown having one port 204. The connector housing 112 can define any suitable number of ports including, for example, one, two, three, four, five, six, seven, eight, or more ports.

The control module connector 144 also includes a plurality of connector contacts, such as connector contact 214, disposed within each port 204. When the elongated device 200 is inserted into the port 204, the connector contacts 214 can be aligned with a plurality of terminals 210 disposed along the proximal end(s) of the elongated device(s) 200 to electrically couple the control module 102 to the electrodes (134 of FIG. 1) disposed at a distal end of the lead 103. Examples of connectors in control modules are found in, for example, U.S. Pat. Nos. 7,244,150 and 8,224,450, which are incorporated by reference.

FIG. 2B is a schematic side view of another embodiment of the electrical stimulation system 100. The electrical stimulation system 100 includes a lead extension 224 that is configured and arranged to couple one or more elongated devices 200 (e.g., the lead body 106, an adaptor, another lead extension, or the like or combinations thereof) to the control module 102. In FIG. 2B, the lead extension 224 is shown coupled to a single port 204 defined in the control module connector 144. Additionally, the lead extension 224 is shown configured and arranged to couple to a single elongated device 200. In alternate embodiments, the lead extension 224 is configured and arranged to couple to multiple ports 204 defined in the control module connector 144, or to receive multiple elongated devices 200, or both.

A lead extension connector 222 is disposed on the lead extension 224. In FIG. 2B, the lead extension connector 222 is shown disposed at a distal end 226 of the lead extension 224. The lead extension connector 222 includes a connector housing 228. The connector housing 228 defines at least one port 230 into which terminals 210 of the elongated device 200 can be inserted, as shown by directional arrow 238. The connector housing 228 also includes a plurality of connector contacts, such as connector contact 240. When the elongated device 200 is inserted into the port 230, the connector contacts 240 disposed in the connector housing 228 can be aligned with the terminals 210 of the elongated device 200 to electrically couple the lead extension 224 to the electrodes (134 of FIG. 1) disposed along the lead (103 in FIG. 1).

In at least some embodiments, the proximal end of the lead extension 224 is similarly configured and arranged as a proximal end of the lead 103 (or other elongated device 200). The lead extension 224 may include a plurality of electrically conductive wires (not shown) that electrically couple the connector contacts 240 to a proximal end 248 of the lead extension 224 that is opposite to the distal end 226. In at least some embodiments, the conductive wires disposed in the lead extension 224 can be electrically coupled to a plurality of terminals (not shown) disposed along the proximal end 248 of the lead extension 224. In at least some embodiments, the proximal end 248 of the lead extension 224 is configured and arranged for insertion into a connector disposed in another lead extension (or another intermediate device). In other embodiments (and as shown in FIG. 2B), the proximal end 248 of the lead extension 224 is configured and arranged for insertion into the control module connector 144.

In at least some instances, a large control module, such as the control module 102 illustrated in FIGS. 1-2B, is not desirable. A smaller, more compact control module may be suitable for situations such as, for example, short-term implantation (for example, 1 or 2 weeks, 1, 2, 3, 4, 6, 8, 12, or 18 months), short-term trial (for example, 1 or 2 weeks, 1, 2, 3, 4, 6, 8, 12, or 18 months), clinical studies (for example, for a period of 1 or 2 weeks, 1, 2, 3, 4, 6, 8, 12, or 18 months), or the like. Such a control module may also be useful when a less invasive surgical implantation is desired, recommended, or required. In some instances, a patient or clinician may be willing to charge the control module more frequently if the control module is smaller or the surgery is less invasive. In addition, there may be more options in the body of the patient for implantation of a smaller control module than are available for the larger control module (which is often implanted in the thoracic body cavity or the buttocks due to the size of the device.) A smaller control module may also be less expensive and particularly useful for trials to determine whether electrical stimulation is beneficial. In at least some embodiments, the electrical stimulation system with the smaller control module can be upgraded to an electrical stimulation system such as that illustrated in FIGS. 1-2B if the trial shows sufficient benefit to the patient. In at least some embodiments, the smaller control module may allow for the device to be Mill (magnetic resonance imaging) conditionally safe because of its implant location and size.

In some embodiments, the control module can be made smaller by permanently affixing the lead (or a lead extension) to the control module. For example, the lead can be hardwired to the stimulation circuitry so that the control module does not need a connector and header.

Figure 3:
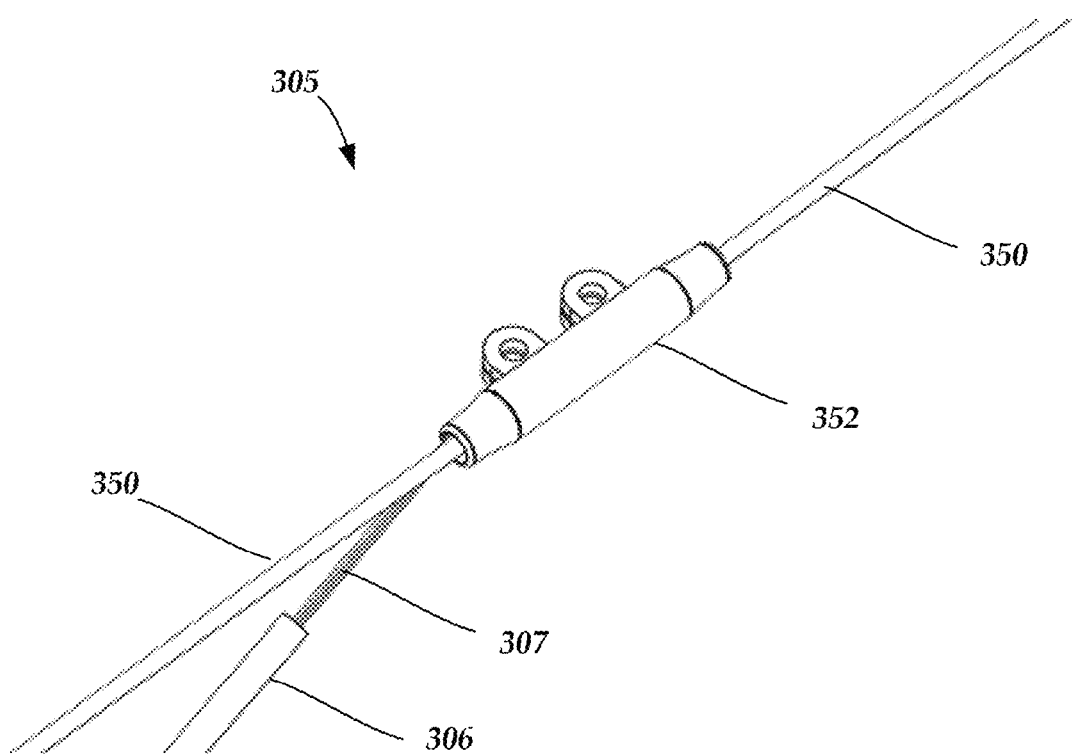
FIG. 3 is a schematic perspective view of a distal end portion of a lead that includes a slotted sleeve stimulation device according to an embodiment of the present invention.

FIG. 3 illustrates, schematically, a distal end portion 305 implanted on a target nerve 350 according to an embodiment of the present invention. The distal end portion 305 includes an electrical stimulation device 352 (hereinafter referred to as a sleeve 352), a lead body 306 and a transition element 307 electrically connecting the sleeve 352 with the lead body 306. In one embodiment, the transition element 307 may take the form of a flexible, ribbon cable to provide strain relief vis-à-vis the lead body 306 and the sleeve 352. The ribbon cables may also be referred to as multi-wire planar cable, which is understood to be a cable with many conducting wires running parallel to each other on the same flat plane, such as ribbon cables used to connect peripherals and other components in the computing industry. The transition element 307 may have a bellowed configuration to allow for the flexibility. The lead body 306 is structurally the same or similar to the lead body 106 (FIG. 1), operates in a same or similar manner, and may be manufactured in accordance with one or more of the methods disclosed herein and disclosed in U.S. Patent Application No. 2007/0150036, which is hereby incorporated by reference in its entirety, or in accordance with other methods or references cited herein.

The lead body 306 and the sleeve 352 can be made from a non-conductive, biocompatible material such as, for example, silicone, polyurethane, polyetheretherketone ("PEEK"), epoxy, and the like or combinations thereof. The lead body 306 and sleeve 352 may be formed in the desired shape by any process including, for example, molding (including injection molding), casting, and the like.

Figure 4:
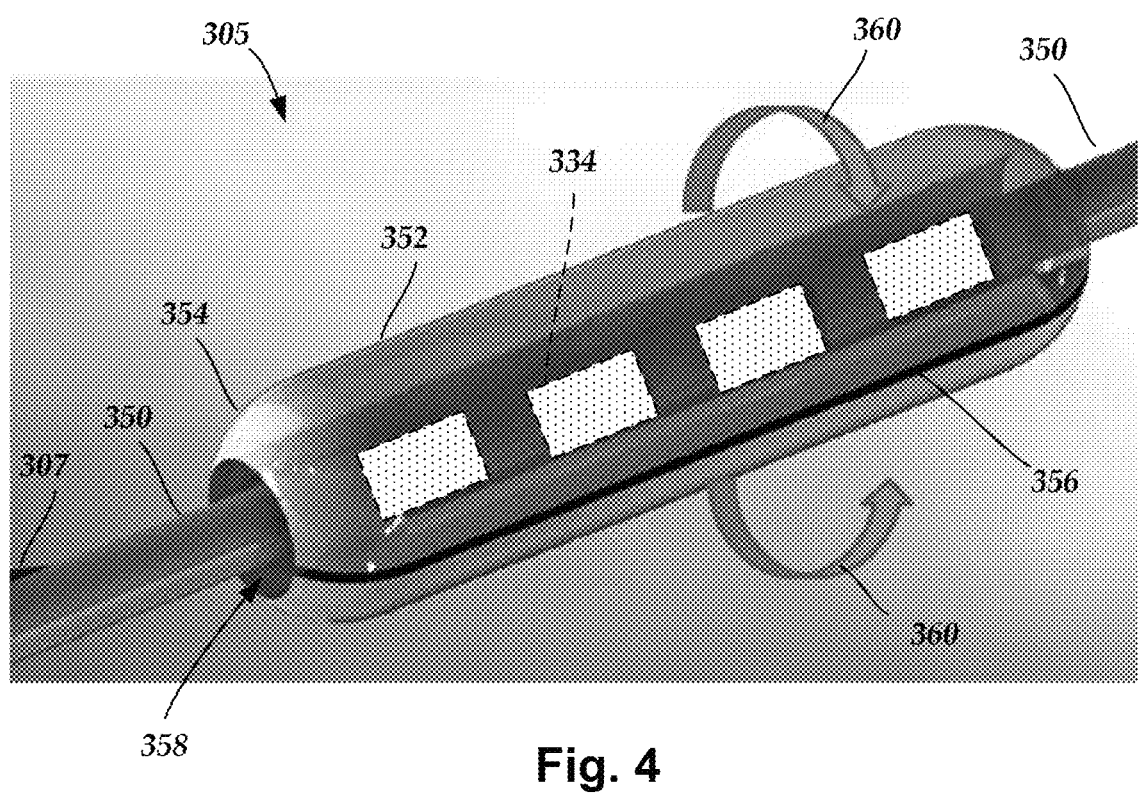
FIG. 4 is a schematic, perspective, close-up view of the slotted sleeve stimulation device of FIG. 3 according to an embodiment of the present invention.

Referring to FIG. 4, the sleeve 352 may permit stimulation of the target nerve 350, for example a vagus or sympathetic nerve, by using a plurality of electrodes 334 disposed into the sleeve 352. By way of example, the sleeve 352 can operate to provide vagus or sympathetic nerve stimulation. When using traditional leads to stimulate the target nerve, it may be difficult to initiate and maintain contact between the traditional lead and the target nerve. In at least some embodiments, the sleeve 352 may advantageously permit an easier implantation around the target nerve than conventional leads that wrap helically around the target nerve. In at least some embodiments, the sleeve 352 may also permit selective stimulation of different regions of the target nerve 350. The number of electrodes 334 as well as the arrangement of the electrodes 334 can vary depending on the type of nerve being stimulated, a region of the nerve being stimulated, or any combination thereof.

In one embodiment, the sleeve 352 is made from silicone, more specifically liquid silicone rubber (LSR), with the electrodes 334 disposed thereon. The sleeve 352 may be manufactured by placing the electrodes 334 onto an LSR pad or carrier and then attaching electrically conductive cables or wires ("conductors")(not shown) to the electrodes 334. Hence, FIG. 4 shows the electrodes 334 in dashed line format.

The electrodes 334 can be formed using any conductive, biocompatible material. Examples of suitable materials include metals, alloys, conductive polymers, conductive carbon, and the like, as well as combinations thereof. In at least some embodiments, one or more of the electrodes 334 are formed from one or more of: platinum, platinum iridium, palladium, palladium rhodium, or titanium. The electrodes 334 may take the form of segmented electrodes, have a variety of shapes such as, but not limited to, a concave, convex or otherwise curved shape, a box shape, a dish or parabolic shape, or any combination thereof. In at least some embodiments, the electrodes 334 may take the form of segmented electrodes having a shape complementary to a body or carrier onto which they are disposed.

Any suitable number of electrodes 334 can be disposed on the sleeve 352 including, for example, four, five, six, seven, eight, nine, ten, eleven, twelve, fourteen, sixteen, twenty-four, thirty-two, or more electrodes 334. The electrodes 334 can be disposed on the sleeve 352 in any suitable arrangement. In at least some embodiments, an inward facing surface of the electrode 334 is flush with an inner surface of the sleeve 352. In yet other embodiments, the inward facing surface of the electrode 334 is recessed relative to the inner surface of the sleeve 352.

The electrodes 334 may be arranged into columns, rows or some combination thereof. In at least some embodiments, one column or row includes two, three, four, five, six, eight or more electrodes 334. The arrangement of the electrode(s) 334 may vary. For example, the electrodes 334 may be arranged in two, three, four or more parallel columns or rows where such columns or rows can be aligned or staggered from one another, or in any other desired column or row arrangement. The electrodes may also be arranged, for example, in a row, or "in line," along the longitudinal axis of a small diameter lead body. Optionally, the electrodes may be placed linearly, circularly, or elliptically. The arrangement of electrodes may be symmetrical or asymmetrical. As will be recognized, other arrangements of electrodes are also possible.

In at least some embodiments, the sleeve 352 is formed into an elongated, cylindrical shape having tapered end portions 354 and a slit 356, wherein the slit 356 may be introduced during the molding process or may be cut, such as, but not limited to, a laser cut, after the molding process. The slit 356 extends for an entire length of the sleeve 352 and extends radially inward through a portion of the sleeve into a nerve channel 358, which is defined by an inner surface of the sleeve 352. In other embodiments, the sleeve 352 can have any shape or cross-section that enables opening and closing of the sleeve 352 during manipulation of the sleeve relative to the target nerve 350. Examples of the suitable cross-sections include, but are not limited to, elliptical, circular, oval, and so forth. Further, the sleeve 352 may have an unsymmetrical shape and structure that permits opening and closing of the sleeve 352. The tapered end portions 354 may advantageously provide more of a gentle transition at each end of the sleeve 352 since the tapered end portions 354 help to make the sleeve less rigid or stiff near each end. In at least some embodiments, the reduced rigidity or stiffness from the tapered end portions 354 may provide strain relief vis-à-vis the target nerve 350. The tapered end portions 354 may take a variety of shapes such as, but not limited to, rounded, sloped, stepped, or otherwise transitioned from the thickness of the sleeve 352 to a free edge of the end portions 354.

In at least some embodiments and during installation around the target nerve 350, the sleeve 352 is opened in a clam shell manner with rotation occurring about a common hinge line opposite the slit 356. In at least some embodiments, the material of the sleeve 352 functions as a common, elastic hinge line allowing the sleeve 352 to rotate from a closed position to an open position, and vice-versa, in the clam shell manner, preferably without permanent deformation (i.e., "elastic") to the sleeve 352. The sleeve 352 is opened by an amount sufficient to allow it to be fed, slid, moved or otherwise transitioned over and onto or removed from the target nerve 350. Once in position over the target nerve 350, the sleeve 352 is closed in a clamshell manner as indicated by rotational arrows 360. The closed position may take the form of sleeve edges adjacent to the slit 356 being urged into physical contact or remaining slightly spaced apart. In the latter situation, a spatial distance between the sleeve edges adjacent to the slit 356 is smaller than a diameter of the target nerve 350, thus retaining the target nerve 350 within the nerve channel 358 of the sleeve 352. The nerve channel 352 is preferably sized to prevent or reduce compression of target nerve 350 by the sleeve 352 when in the closed position.

Figure 5:
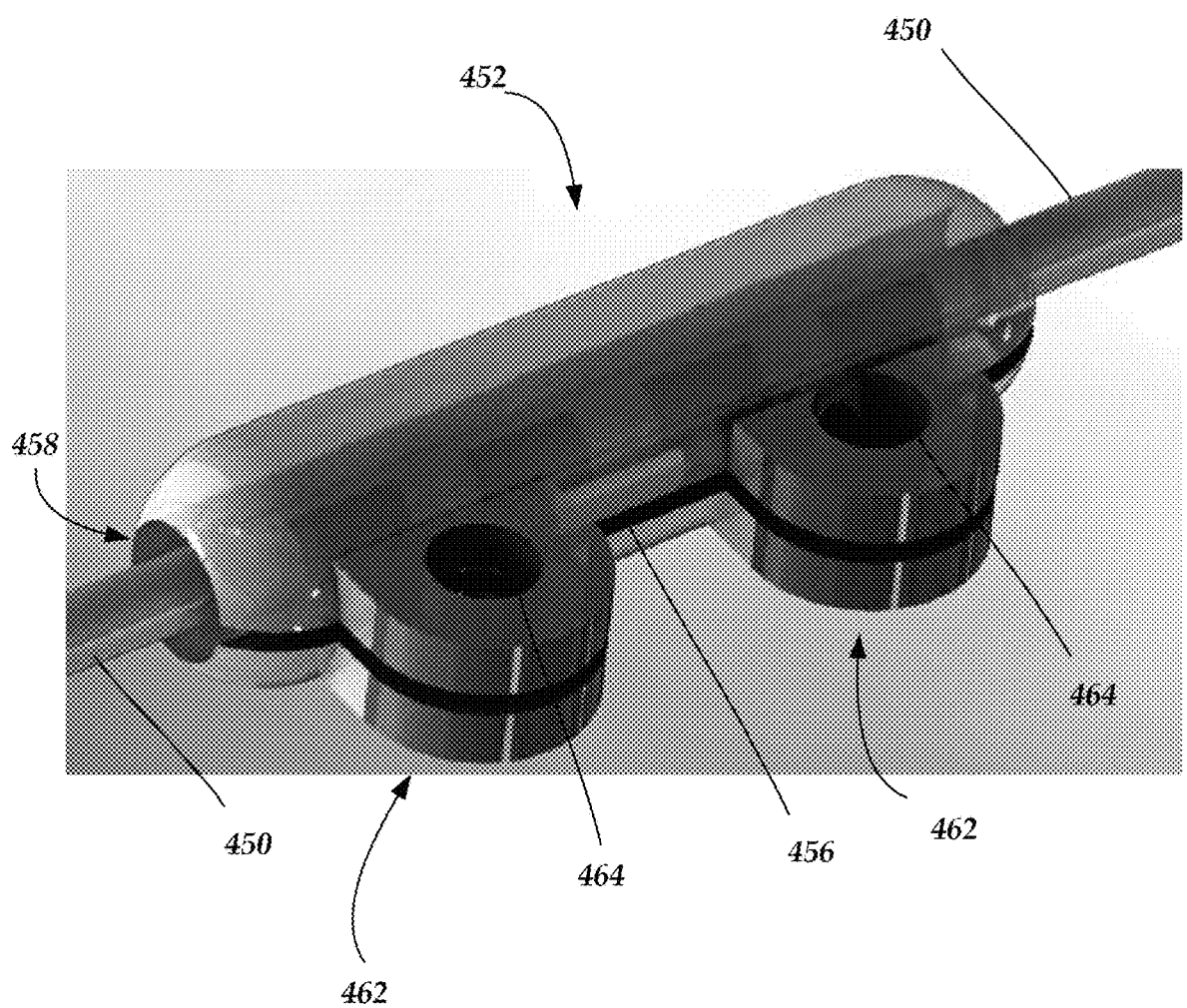
FIG. 5 is a schematic, perspective, close-up view of a slotted sleeve stimulation device with suture blocks according to another embodiment of the present invention.

FIG. 5 shows, schematically, a sleeve 452 implanted and closed upon on a target nerve 450 according to at least some embodiments. In at least some embodiments, the sleeve 452 includes suture eyelets or tabs 462 having suture holes 464 that can be pre-made or pre-formed during molding of the sleeve 452. The suture tabs 462 extend from the sleeve 452 and may approximate the shape of a pillow block, but a variety of other shapes are also contemplated. The illustrated embodiment shows two suture tabs 462, but the sleeve 452 may have a single suture tab 462 or more than two suture tabs 462. A slit 456 extends through the suture tabs 462 and through one side of the sleeve 452 and into a nerve channel 458 defined by the sleeve 452. The extended suture tabs 462 permit the sleeve 452 to be anchored (e.g., sutured) to the patient's tissue without the need to wrap a suture around the sleeve 452. The suture tabs 462 may advantageously permit closing and anchoring of the sleeve 452 without undesirably compressing the sleeve 452 around the target nerve.

During implantation, the sleeve 452 is opened and slid over the target nerve 450 (similar to the previous embodiment of FIG. 3), closed, and then sutured to a patient's tissue. The suture tabs 462 may be located on areas of the sleeve 452 that would not necessitate making a slit through the suture tabs 462. In at least some embodiments, the suture tabs 462 may be made out of the same material of the sleeve 452, a different material (e.g., stiffer or stronger material), embedded with stiffening elements (not shown), or any combination thereof. Further, the suture tabs 462 may attached to the sleeve 452 after the molding process or may be formed integrally with the sleeve 452 during the molding process.

Figure 6:
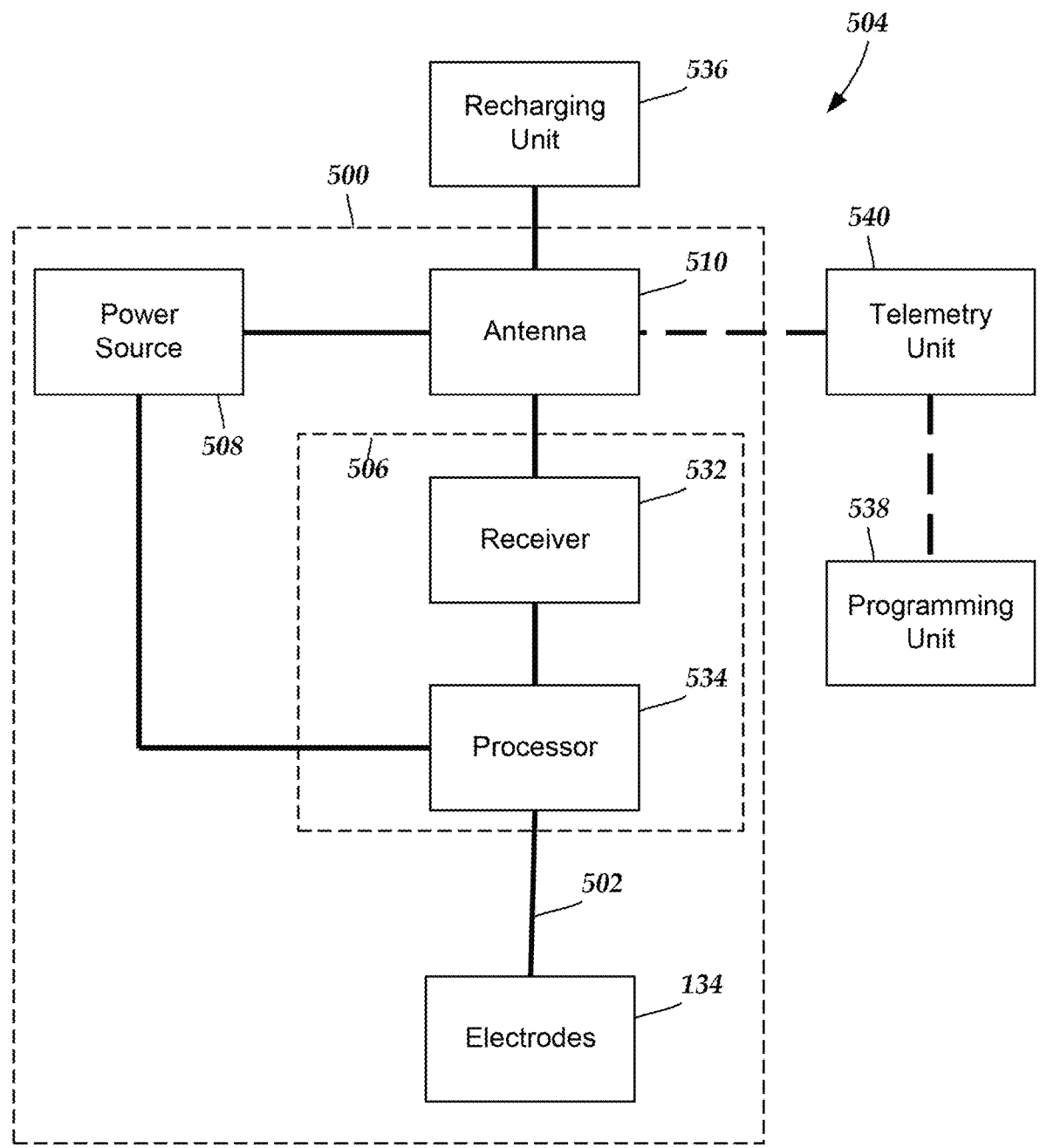
FIG. 6 is a schematic overview of one embodiment of components of an electrical stimulation arrangement according to an embodiment of the present invention.

FIG. 6 is a schematic overview of one embodiment of components of an electrical stimulation arrangement 504 that includes an electrical stimulation system 500 with a lead 502, stimulation circuitry 506, a power source 508, and an antenna 510. The electrical stimulation system can be, for example, any of the electrical stimulation systems described above. It will be understood that the electrical stimulation arrangement can include more, fewer, or different components and can have a variety of different configurations including those configurations disclosed in the stimulator references cited herein.

If the power source 508 is a rechargeable battery or chargeable capacitor, the power source may be recharged/ charged using the antenna 510, if desired. Power can be provided for recharging/charging by inductively coupling the power source 508 through the antenna 510 to a recharging unit 536 external to the user. Examples of such arrangements can be found in the references identified above.

In one embodiment, electrical current is emitted by the electrodes (such as electrodes 134 in FIG. 1) on the lead 502 to stimulate nerve fibers, muscle fibers, or other body tissues near the electrical stimulation system. The stimulation circuitry 506 can include, among other components, a processor 534 and a receiver 532. The processor 534 is generally included to control the timing and electrical characteristics of the electrical stimulation system. For example, the processor 534 can, if desired, control one or more of the timing, frequency, strength, duration, and waveform of the pulses. In addition, the processor 534 can select which electrodes can be used to provide stimulation, if desired. In some embodiments, the processor 534 selects which electrode(s) are cathodes and which electrode(s) are anodes. In some embodiments, the processor 534 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 538 that, for example, allows modification of pulse characteristics. In the illustrated embodiment, the processor 534 is coupled to a receiver 532 which, in turn, is coupled to the antenna 510. This allows the processor 534 to receive instructions from an external source to, for example, direct the pulse characteristics and the selection of electrodes, if desired.

In one embodiment, the antenna 510 is capable of receiving signals (e.g., RF signals) from an external telemetry unit 540 that is programmed by the programming unit 538. The programming unit 538 can be external to, or part of, the telemetry unit 540. The telemetry unit 540 can be a device that is worn on the skin of the user or can be carried by the user and can have a form similar to a pager, cellular phone, or remote control, if desired. As another alternative, the telemetry unit 540 may not be worn or carried by the user but may only be available at a home station or at a clinician's office. The programming unit 538 can be any unit that can provide information to the telemetry unit 540 for transmission to the electrical stimulation system 500. The programming unit 538 can be part of the telemetry unit 540 or can provide signals or information to the telemetry unit 540 via a wireless or wired connection. One example of a suitable programming unit is a computer operated by the user or clinician to send signals to the telemetry unit 540.

The signals sent to the processor 534 via the antenna 510 and the receiver 532 can be used to modify or otherwise direct the operation of the electrical stimulation system 500. For example, the signals may be used to modify the pulses of the electrical stimulation system such as modifying one or more of pulse duration, pulse frequency, pulse waveform, and pulse strength. The signals may also direct the electrical stimulation system 500 to cease operation, to start operation, to start charging the battery, or to stop charging the battery.

Optionally, the electrical stimulation system 500 may include a transmitter (not shown) coupled to the processor 534 and the antenna 510 for transmitting signals back to the telemetry unit 540 or another unit capable of receiving the signals. For example, the electrical stimulation system 500 may transmit signals indicating whether the electrical stimulation system 500 is operating properly or not or indicating when the battery needs to be charged or the level of charge remaining in the battery. The processor 534 may also be capable of transmitting information about the pulse characteristics so that a user or clinician can determine or verify the characteristics.

The above specification provides a description of the structure, manufacture, and use of the invention. Since many embodiments of the invention can be made without departing from the spirit and scope of the invention, the invention also resides in the claims hereinafter appended.

What is claimed as new and desired to be protected by Letters Patent of the United States is:

1. An electrical stimulation lead for stimulating a target nerve, the electrical stimulation lead comprising:
an elongated sleeve having a first portion and a second portion, the first portion hingedly coupled to the second portion, the elongated sleeve having an inner surface that continually extends from the first portion to the second portion and an outer surface that continually extends from the first portion to the second portion, the inner surface defining a nerve channel to receive the target nerve, the elongated sleeve further having a longitudinal slit extending from the outer surface to the nerve channel, the longitudinal slit extending along an entire length of the elongated sleeve, wherein a section of the first portion hingedly moves relative to a section of the second portion to receive the target nerve into the nerve channel, wherein the elongated sleeve includes tapered end portions;
a plurality of electrodes disposed on the inner surface of the elongated sleeve;
a lead body;
a plurality of conductors extending along the lead body; and
a ribbon cable extending from the elongated sleeve and attached to the lead body to electrically couple the conductors extending along the lead body to the plurality of electrodes, wherein the ribbon cable includes a bellowed portion for strain relief.

2. The electrical stimulation lead of claim 1, wherein the section of the first portion rotates relative to the section of the second portion relative to a common hinge line located opposite the longitudinal slit.

3. The electrical stimulation lead of claim 2, wherein material along the common hinge line remains in a mechanically elastic range when the elongated sleeve is moved from a closed position to an open position.

4. The electrical stimulation lead of claim 1, further comprising at least one suture tab extending from the elongated sleeve.

5. The electrical stimulation lead of claim 4, wherein the at least one suture tab includes a pre-made suture hole.

6. The electrical stimulation lead of claim 4, wherein the at least one suture tab includes a suture slit that cooperates with the longitudinal slit of the elongated sleeve.

7. The electrical stimulation lead of claim 1, wherein the plurality of electrodes have a shape complementary to the inner surface of the elongated sleeve.

8. The electrical stimulation lead of claim 1, wherein a width of the longitudinal slit is configured to retain the target nerve within the nerve channel when the elongated sleeve is in a closed position and configured to receive or release the target nerve when the elongated sleeve is in an open position.

9. The electrical stimulation lead of claim 1, wherein the plurality of electrodes are arranged in two or more parallel rows or columns.

10. The electrical stimulation lead of claim 1, wherein an inward facing surface of each of the electrodes is flush with the inner surface of the elongated sleeve.

11. The electrical stimulation lead of claim 1, wherein an inward facing surface of each of the electrodes is recessed relative to the inner surface of the elongated sleeve.

12. An electrical stimulation system comprising:
the electrical stimulation lead of claim 1;
a control module coupleable to the electrical stimulation lead, the control module comprising
a housing, and
an electronic subassembly disposed in the housing; and
a connector for receiving the electrical stimulation lead, the connector having a proximal end, a distal end, and a longitudinal length, the connector comprising
a connector housing defining a port at the distal end of the connector, the port configured and arranged for receiving a proximal end of the lead body of the electrical stimulation lead, and
a plurality of connector contacts disposed in the connector housing, a plurality of connector contacts configured and arranged to couple to at least one of a plurality of terminals disposed on the proximal end of the lead body of the electrical stimulation lead.

13. The electrical stimulation system of claim 12, further comprising a lead extension coupleable to both the electrical stimulation lead and the control module.

14. The electrical stimulation system of claim 12, further comprising at least one suture tab extending from the elongated sleeve.

15. The electrical stimulation system of claim 14, wherein the at least one suture tab includes a suture slit that cooperates with the longitudinal slit of the elongated sleeve, wherein the suture slit separates one of the at least one suture tab into two separate portions that are each attached to a different portion of the elongated sleeve and align with each other when the elongated sleeve is in a closed position.

16. An electrical stimulation lead for stimulating a target nerve, the electrical stimulation lead comprising:
an elongated sleeve having a first portion and a second portion, the first portion hingedly coupled to the second portion, the elongated sleeve having an inner surface that continually extends from the first portion to the second portion and an outer surface that continually extends from the first portion to the second portion, the inner surface defining a nerve channel to receive the target nerve, the elongated sleeve further having a longitudinal slit extending from the outer surface to the nerve channel, the longitudinal slit extending along an entire length of the elongated sleeve, wherein a section of the first portion hingedly moves relative to a section of the second portion to receive the target nerve into the nerve channel, wherein the elongated sleeve includes tapered end portions;
a plurality of electrodes disposed on the inner surface of the elongated sleeve;
a lead body;
a plurality of conductors extending along the lead body;
a ribbon cable extending from the elongated sleeve and attached to the lead body to electrically couple the conductors extending along the lead body to the plurality of electrodes; and
at least one suture tab extending from the elongated sleeve, wherein the at least one suture tab includes a suture slit that cooperates with the longitudinal slit of the elongated sleeve, wherein the suture slit separates at least one of the at least one suture tab into two separate portions that are each attached to a different portion of the elongated sleeve and align with each other when the elongated sleeve is in a closed position.

17. The electrical stimulation lead of claim 16, wherein each of the two separate portions of the at least one of the at least one suture tab includes a suture hole.

18. The electrical stimulation lead of claim 17, wherein the suture holes of the two separate portions align with each other when the elongated sleeve is in a closed position.

19. An electrical stimulation system comprising:
the electrical stimulation lead of claim 16;
a control module coupleable to the electrical stimulation lead, the control module comprising
   a housing, and
   an electronic subassembly disposed in the housing; and
a connector for receiving the electrical stimulation lead, the connector having a proximal end, a distal end, and a longitudinal length, the connector comprising
   a connector housing defining a port at the distal end of the connector, the port configured and arranged for receiving a proximal end of the lead body of the electrical stimulation lead, and
a plurality of connector contacts disposed in the connector housing, a plurality of connector contacts configured and arranged to couple to at least one of a plurality of terminals disposed on the proximal end of the lead body of the electrical stimulation lead.

20. The electrical stimulation system of claim 19, wherein the ribbon cable includes a bellowed portion for strain relief.

* * * * *